US012673971B2

(12) United States Patent    (10) Patent No.:    US 12,673,971 B2
Akizawa et al.                   (45) Date of Patent:    Jul. 7, 2026

(54) AMYLOID-β AGGREGATION INHIBITOR, PHARMACEUTICAL COMPOSITION FORAMYLOID-β AGGREGATION DISEASE, AND USE APPLICATION OF SAME

(71) Applicant: O-FORCE CO., LTD, Hata-gun (JP)

(72) Inventors: Toshifumi Akizawa, Kochi (JP); Motoaki Saito, Kochi (JP); Youichirou Higashi, Kochi (JP); Rina Nakamura, Kochi (JP)

(73) Assignee: O-FORCE CO., LTD, Kochi (JP)

( * ) Notice:   Subject to any disclaimer, the term of this patent is extended or adjusted under 35 U.S.C. 154(b) by 557 days.

(21) Appl. No.:   18/247,584

(22) PCT Filed:   Oct. 1, 2021

(86) PCT No.:   PCT/JP2021/036466
     § 371 (c)(1),
     (2) Date:   Mar. 31, 2023

(87) PCT Pub. No.:   WO2022/071591
     PCT Pub. Date: Apr. 7, 2022

(65)              Prior Publication Data
     US 2023/0374070 A1      Nov. 23, 2023

(30)         Foreign Application Priority Data
     Oct. 2, 2020    (JP) ................................. 2020-167404

(51) Int. Cl.
     *C07K 7/06*        (2006.01)
     *A61K 38/00*       (2006.01)
     *A61K 49/00*       (2006.01)
     *A61P 25/28*       (2006.01)
(52) U.S. Cl.
     CPC ............ *C07K 7/06* (2013.01); *A61K 49/0008* (2013.01); *A61P 25/28* (2018.01); *A61K 38/00* (2013.01)
(58) Field of Classification Search
     None
     See application file for complete search history.

(56)              References Cited

U.S. PATENT DOCUMENTS

|  |  |  |  |  |
|---|---|---|---|---|
| 6,753,413 | B1 | 6/2004 | Ching et al. | |
| 7,244,764 | B2 | 7/2007 | Kong et al. | |
| 7,414,076 | B2 | 8/2008 | Kong et al. | |
| 10,995,119 | B2 | 5/2021 | Akizawa et al. | |
| 2005/0038117 | A1 | 2/2005 | Kong et al. | |
| 2005/0096385 | A1 | 5/2005 | Kong et al. | |
| 2019/0023741 | A1* | 1/2019 | Akizawa ................ | C07K 14/47 |
| 2020/0140506 | A1 | 5/2020 | Skretas | |

FOREIGN PATENT DOCUMENTS

| EP | 1 548 108 | 6/2005 |
|---|---|---|
| JP | 2004-313101 | 11/2004 |
| JP | 2007-516939 | 6/2007 |
| WO | 2004/058239 | 7/2004 |
| WO | 2004/058258 | 7/2004 |
| WO | 2004/112762 | 12/2004 |
| WO | 2004/113275 | 12/2004 |
| WO | 2004/113277 | 12/2004 |
| WO | 2004/113391 | 12/2004 |
| WO | 2005/000288 | 1/2005 |
| WO | 2005/000406 | 1/2005 |
| WO | 2007/049098 | 5/2007 |
| WO | 2016/042411 | 3/2016 |
| WO | 2017/119511 | 7/2017 |
| WO | 2020/117031 | 6/2020 |

OTHER PUBLICATIONS

Uniprot Q7M458 • DGP_CORAP. Dart gland peptide from Cornu aspersum. Downloaded Sep. 25, 2025. (Year: 2025).*
Uniprot A0A2K3MLVO • A0A2K3MLVO_TRIPR. Protein from Trifolium pratense. Downloaded Sep. 25, 2025. (Year: 2025).*
Nakamura, et al., "Five-mer peptides, inhibitor of amyloid-beta 25-35 aggregation, improve short-term memory deficits in amyloid-beta 25-35-induced Alzheimer's model mice", Journal of the Neurological Sciences, 2023, vol. 455, p. 121429.
Nakamura, et al., "Five-mer peptides prevent short-term spatial memory deficits in Aβ25-35-induced Alzheimer's model mouse by suppressing Aβ25-35 aggregation and resolving its aggregate form", Alzheimer's Research & Therapy, 2023, vol. 15, 9 pages.
Extended European Search Report issued in corresponding European Patent Application No. 21875887.8, Nov. 13, 2024, 7 pages.
Rouault et al., "Interaction of BTG1 and p53-regulated BTG2 Gene Products with mCaf1, the Murine Homolog of a Component of the Yeast CCR4 Transcriptional Regulatory Complex", The Journal of Biological Chemistry, 1998, vol. 273, No. 35, pp. 22563-22569.
Yang et al., "Crystal structures of human BTG2 and mouse TIS21 involved in suppression of CAF1 deadenylase activity", Nucleic Acids Research, 2008, vol. 36, No. 21, pp. 6872-6881.
Hatakawa et al., "A Fragment peptide derived from Box A domain of ANA Protein Cleaves Amyloid β Protein", The 29th Symposium on Biomedical-Analytical Sciences [Online], Jul. 25, 2016, [Date of Search: Mar. 14, 2017], p. 19, Internet: URL:http://www.pharm. kyotou.ac.jp/seizai/bmas2016/doc/BMAS2016プログラム.pdf **The subject matter presented in the afore-mentioned Symposium is that of the priority application for the current application.

(Continued)

*Primary Examiner* — Christina Bradley
(74) *Attorney, Agent, or Firm* — HSML P.C.

(57)              ABSTRACT

A drug that inhibits aggregation of amyloid-β, which causes Alzheimer's disease and the like. The amyloid-βaggregation inhibitor is characterized by containing at least one of a peptide having an amino acid sequence of SEQ ID NO: 1 (GSGNR) or a peptide having an amino acid sequence of SEQ ID NO: 2 (GSGFK). A pharmaceutical composition for an amyloid-βaggregation disease is characterized by containing at least one of a peptide having an amino acid sequence of SEQ ID NO: 1 (GSGNR), and a peptide having an amino acid sequence of SEQ ID NO: 2 (GSGFK).

12 Claims, 7 Drawing Sheets

Specification includes a Sequence Listing.

(56)          References Cited

OTHER PUBLICATIONS

Taniguchi et al., "Affinity of catalytic peptides to the B-amyloid peptides", The 29th Symposium on Biomedical Analytical Sciences [Online], Jul. 25, 2016, [Date of Search: Mar. 14, 2017], p. 20, Internet: URL:http://www.pharm.kyotou.ac.jp/seizai/bmas2016/doc/BMAS2016プログラム.pdf **The subject matter presented in the afore-mentioned Symposium is that of the priority application for the current application.

Extended European Search Report issued in European Patent Application No. 17736048.4, Jun. 24, 2019, 5 pages.

Torkova, et al., "Structure-Functional Study of Tyrosine and Methionine Dipeptides: An Approach to Antioxidant Activity Prediction", Int. J. Mol. Sci. 2015, 16, 25353-25376.

Chan, et al., "Modification of N-Terminal a-Amino Groups of Peptides and Proteins Using Ketenes", J. Am. Chem. Soc. 2012, 134, 2589-2598.

Kung, et al., "N-terminal a-amino group modificatio of peptides by an oxime formation-exchange reaction sequence", Chem.Commun., 2013, 49, 6888-6890.

Nakamura et al., "Evaluation of the proteolyticactivity of 5-mer peptides in BoxA region ofTob/BTG family proteins against Amyloid-βfragment peptides", Peptide Science 2019 Proceedingof the 56th Japanese Peptide Symposium, 2020, 02,pp. 9-10.

International Search Report issued in International Application No. PCT/JP2021/036466, Dec. 21, 2021, 7 pages w/translation.

Written Opinion issued in International Application No. PCT/JP2021/036466, Dec. 21, 2021, 4 pages.

Nakamura, et al., "The discovery of shorter synthetic proteolytic peptides derived from Tob1 protein", Peptides, 2019, vol. 116, pp. 71-77.

Notification of Reason(s) for Rejection of the corresponding Japanese Patent Application (JP2020-167404) dated Jul. 8, 2024, 8 pages w/translation.

* cited by examiner (A)

(B)

(A)

(B)

1

AMYLOID-β AGGREGATION INHIBITOR, PHARMACEUTICAL COMPOSITION FORAMYLOID-β AGGREGATION DISEASE, AND USE APPLICATION OF SAME

SEQUENCE LISTING

The present application is being filed with a Sequence Listing in electronic format. The Sequence Listing is provided as a file entitled "Sequence_Listing_0028.txt" created on Mar. 31, 2023, which is 1282 bytes in size. The information in the electronic format of the Sequence Listing is incorporated herein by reference in its entirety.

TECHNICAL FIELD

The present invention relates to an amyloid-β aggregation inhibitor, a pharmaceutical composition for an amyloid-β aggregation disease, and a use application of the same.

BACKGROUND ART

Alzheimer's disease, which predominantly occurs in old age, has become a serious issue due to the increasing proportion of the elderly in the population as a result of rising life expectancy. Alzheimer's is a progressive central neurodegenerative disease that results in cognitive dysfunction and memory loss. This disease is thought to be caused by fibrillar aggregates (amyloid fibrils) generated by aggregation of amyloid-β through intermolecular association in the brain. However, no clinically effective drugs have been implemented into practice, and further investigation of candidate drugs is required. This issue is not limited to Alzheimer's, but applies to all diseases caused by amyloid fibers.

SUMMARY OF INVENTION

Technical Problem

It is an object of the present invention to provide a novel drug that inhibits aggregation of amyloid-β, which causes Alzheimer's and the like.

Solution to Problem

The present invention is directed to an amyloid-β aggregation inhibitor characterized by containing at least one of a peptide having an amino acid sequence of SEQ ID NO: 1 and a peptide having an amino acid sequence of SEQ ID NO: 2.

SEQ ID NO: 1: GSGNR
SEQ ID NO: 2: GSGFK

The present invention is directed to a pharmaceutical composition for an amyloid-β aggregation disease, characterized by containing at least one of a peptide having an amino acid sequence of SEQ ID NO: 1 and a peptide having an amino acid sequence of SEQ ID NO: 2.

The present invention is directed to a method for inhibiting aggregation of amyloid-β, characterized by including adding the amyloid-β aggregation inhibitor of the present invention to a test subject.

The present invention is directed to a method for treating an amyloid-β aggregation disease, characterized by including administering the amyloid-β aggregation inhibitor of the present invention to a test subject.

Advantageous Effects of Invention

The amyloid-β aggregation inhibitor of the present invention can inhibit the aggregation of amyloid-β through intermolecular association, thus enabling treatment, e.g., prevention, inhibition of progression, and amelioration, of amyloid aggregation diseases such as Alzheimer's.

DESCRIPTION OF EMBODIMENTS

<Amyloid-β Aggregation Inhibitor>

Figure 1:
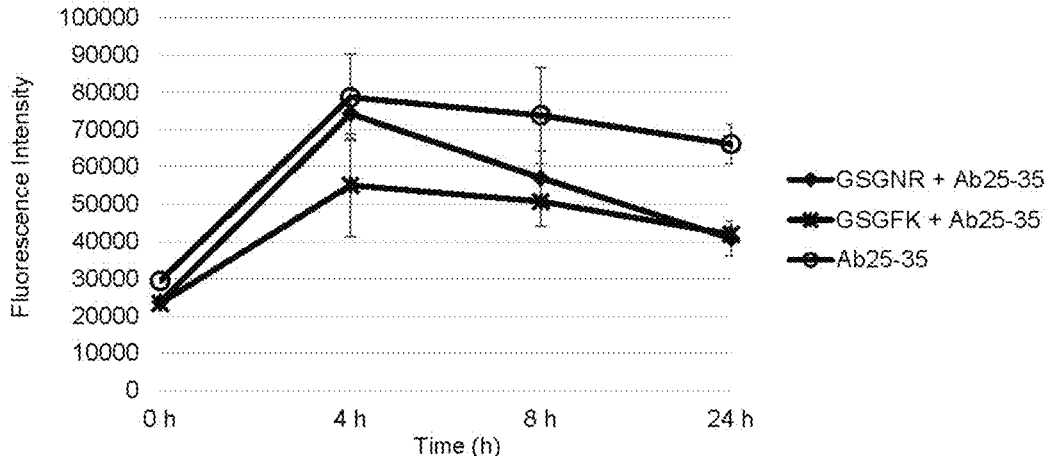
FIG. 1 is a graph showing the fluorescence intensities of reaction solutions to which Peptide 1 (GSGNR (SEQ ID NO: 1)) or Peptide 2 (GSGFK (SEQ ID NO: 1)) was added.

As described above, the amyloid-β aggregation inhibitor of the present invention is characterized by containing at least one of a peptide having an amino acid sequence of SEQ ID NO: 1 and a peptide having an amino acid sequence of SEQ ID NO: 2. The peptide of SEQ ID NO: 1 is hereinafter also referred to as Peptide 1 or GSGNR, and the peptide of SEQ ID NO: 2 is hereinafter also referred to as Peptide 2 or GSGFK.

SEQ ID NO: 1: GSGNR
SEQ ID NO: 2: GSGFK

Peptide 1 and Peptide 2 have constituent units that are amino acid residues that may be, for example, only in the D-form, only in the L-form, or in both the D-form and the L-form.

Peptide 1 and Peptide 2 may be, for example, chemically modified peptide isosters. The chemical modification may be performed, for example, on all of the amino acid residues or some of the amino acid residues. There is no particular limitation on the type of chemical modification, and examples thereof include substitution of hydrogen atoms with halogen atoms, substitution with non-naturally occurring amino acids corresponding to naturally occurring amino acids, introduction of methyl groups, modification of amino acid side chains, cyclization of peptides, modification of carboxyl groups and/or amino groups, and amidation of terminal carboxyl groups.

Peptide 1 and Peptide 2 can inhibit the aggregation of amyloid-β (hereinafter also referred to as Aβ) or fragment peptides thereof. That is to say it is possible to inhibit the aggregation itself of amyloid-β (Aβ) or fragment peptides thereof through intermolecular association, and thus this effect can be said to be, for example, inhibition of the formation of aggregates. There is no particular limitation on the source of amyloid-β whose aggregation is inhibited by Peptide 1 and Peptide 2, and examples thereof include a human and a non-human animal, with the source preferably being a human. The length of the full-length amino acid sequence of human amyloid-β is, for example, the length corresponding to 40 to 42 amino acid residues. The length of the full-length amino acid sequence of human amyloid-β depends, for example, on the site of enzymatic cleavage from the amyloid precursor (APP). The human amyloid-β constituted by 42 amino acid residues is registered in the database (PubChem) under accession number CID: 57339251 and is represented by, for example, SEQ ID NO: 3. The human amyloid-β constituted by 40 amino acid residues is a sequence from the $1^{st}$ amino acid residue (D) at the N-terminus to the $40^{th}$ amino acid residue (V) in SEQ ID NO: 3, and the $40^{th}$ amino acid residue is the C-terminus.

SEQ ID NO: 3: DAEFRHDSGYEVHHQKLVFFAE-DVGSNKGAIIGLMVGGVVIA

The aggregation inhibitor of the present invention can be used to treat diseases (amyloid-β aggregation diseases) that are caused by, for example, aggregation of amyloid-β (Aβ) or fragment peptides thereof. In the present invention, treatment includes the meaning of prevention, inhibition of progression, and amelioration (alleviation), for example, and the aggregation inhibitor is particularly useful for prevention and inhibition of progression because it can inhibit the formation of aggregates itself. Prevention includes, for example, the meaning of prevention of recurrence. There is no particular limitation on the amyloid-β aggregation diseases, and examples thereof include diseases that can be caused by the aggregation of amyloid-β, and specifically include memory impairment, Alzheimer's, and cerebral amyloid angiopathy.

The aggregation inhibitor of the present invention is also referred to as an agglutination inhibiting composition of the present invention. The aggregation inhibitor of the present invention contains at least one of Peptide 1 and Peptide 2 as an active component. The active component contained in the aggregation inhibitor of the present invention may be Peptide 1 alone, Peptide 2 alone, or both Peptide 1 and Peptide 2. The aggregation inhibitor of the present invention may be, for example, a composition containing only the active component or a composition containing the active component and other additive components. There is no particular limitation on the additive components, and examples thereof include pharmacologically acceptable components. As for the additive components, reference can be made, for example, to the following descriptions regarding the pharmaceutical composition.

The aggregation inhibitor of the present invention can be used, for example, in environments in which amyloid-β (Aβ) or fragment peptides thereof are present or are presumed to be present. The aggregation inhibitor of the present invention, for example, can be added to a test subject. The test subject may be a non-living-being-derived test subject that does not contain cells and the like, or a living-being-derived test subject that is cells such as brain cells, tissue such as brain tissue, or an organism. In the case of the latter test subject, the addition of the aggregation inhibitor can be, for example, performed in vivo or in vitro. The cells and tissue may be sourced from a human or a non-human animal, for example, and the organism may be, for example, a human or a non-human animal. Examples of the non-human animal include mammalian animals such as mice, rats, rabbits, horses, sheep, cattle, and camels.

In the present invention, aggregation inhibition is, for example, inhibition (reducing) of amyloid-β aggregation, or inhibition (reducing) through dissociation of amyloid-β aggregates that have already been formed. Peptide 1 (GSGNR (SEQ ID NO: 1)) of the present invention may be, for example, capable of dissociating amyloid-β aggregates and inhibiting aggregation itself. Peptide 2 (GSGFK (SEQ ID NO: 2)) of the present invention may be, for example, capable of inhibiting amyloid-β aggregation itself and dissociating amyloid-β aggregates. The dissociation of amyloid-β aggregates means breaking the aggregates up into simple components, i.e., amyloid-β, for example, and excludes the meaning of degradation through cleavage in amyloid-β molecules, for example, in the amyloid-β aggregates (cleavage of amyloid-β by hydrolysis). In this case, the aggregation inhibitor of the present invention can be, for example, said to be an aggregation dissociating agent. The inhibition of amyloid-β aggregation itself is particularly preferable for prevention, inhibition of progression, amelioration, and the like, for example, and the dissociation of amyloid-β aggregates is particularly preferable, for example, for inhibition of progression, amelioration, and the like.

The aggregation inhibitor of the present invention may contain, for example, an additional peptide in addition to Peptide 1 and/or Peptide 2. The additional peptide may be, for example, in a form that is bonded to Peptide 1 or Peptide 2. The additional peptide may have, for example, a DDS ability to the site in which amyloid-β or amyloid-β aggregates are present. Furthermore, the additional peptide may be, for example, a signal peptide that is bonded to Peptide 1 or Peptide 2 at the time of administration to an organism and is cleaved from Peptide 1 or Peptide 2 by an enzyme or the like in the organism after administration to the organism.

The aggregation inhibitor of the present invention can be used, for example, also as a later-described pharmaceutical composition for an amyloid-β aggregation disease of the present invention. Furthermore, the aggregation inhibitor of the present invention can be used, for example, in a later-described method for inhibiting amyloid-β aggregation of the present invention and method for treating an amyloid-β aggregation disease. As for the aggregation inhibitor of the present invention, reference can be made to the following descriptions regarding the pharmaceutical composition for an amyloid-β aggregation disease, the method for inhibiting aggregation of amyloid-β, and the method for treating an amyloid-β aggregation disease of the present invention.

<Pharmaceutical Composition for Amyloid-β Aggregation Disease>

As described above, the pharmaceutical composition for an amyloid-β aggregation disease of the present invention (hereinafter also referred to as a pharmaceutical composition) is characterized by containing at least one of Peptide 1 having an amino acid sequence of SEQ ID NO: 1 and Peptide 2 having an amino acid sequence of SEQ ID NO: 2.

The pharmaceutical composition of the present invention is characterized by containing at least one of Peptide 1 and Peptide 2 that can inhibit the aggregation of amyloid-β or fragment peptides thereof, and there is no particular limitation on the other aspects of the configuration. As for Peptide 1 and Peptide 2, reference can be made to the foregoing descriptions regarding the aggregation inhibitor of the present invention.

The pharmaceutical composition of the present invention contains at least one of Peptide 1 and Peptide 2 as an active component. The active component contained in the pharmaceutical composition of the present invention may be Peptide 1 alone, Peptide 2 alone, or both Peptide 1 and Peptide 2, and may further include other active components on the amyloid-β aggregation diseases. The other active components may be an active component that inhibits the formation of aggregates or an active component that degrades aggregates that have been formed as with Peptide 1 and Peptide 2, for example, the latter being preferred. The degradation of aggregates may be, for example, degradation through cleavage of the aggregates using hydrolytic activity or the like, or degradation through dissociation of the aggregates into constituent molecules thereof (amyloid-β or fragment peptides thereof). Examples of the active component that degrades the aggregates through cleavage include a catalytic peptide that exhibits hydrolytic activity as disclosed in WO 2017/119511A, which is herein incorporated by reference. The pharmaceutical composition of the present invention particularly preferably contains an active component that inhibits the formation of aggregates itself (Peptide 1 and/or Peptide 2) and an active component that degrades the aggregates, for example, because the former inhibits the formation of aggregates itself, and, even if aggregates are formed, the latter can degrade aggregates that have been formed, and thus it is possible to provide double defense.

The pharmaceutical composition of the present invention may be, for example, a composition containing only the active component or a composition containing the active component and other additive components. There is no particular limitation on the additive components, and examples thereof include pharmacologically acceptable components. The additive components may be, for example, set as appropriate according to the administration method, the administration site, the dosage form, and the like of the pharmaceutical composition of the present invention.

There is no particular limitation on the administration method of the pharmaceutical composition of the present invention, and examples thereof include parenteral administration and oral administration. Parenteral administration may be, for example, intravenous administration.

Examples of parenteral administration include administration by injection at an affected site, intravenous injection, subcutaneous injection, intradermal injection, and intravenous drip injection, nasal administration, and dermal administration. In the case of parenteral administration, there is no particular limitation on the administration site, and the pharmaceutical composition may be, for example, directly administered to a treatment site or indirectly administered to a treatment site. In the latter case, the administration site, for example, is a site from which the active component of the pharmaceutical composition of the present invention can be delivered to the treatment site. In many cases, amyloid-β aggregation diseases are caused by, for example, aggregation of amyloid-β in the brain, as in the case of memory impairment and Alzheimer's mentioned above. Thus, the treatment site is the brain, for example, and the administration method is preferably direct administration to the brain, for example, by injection, nasal administration, or the like.

There is no particular limitation on the dosage form of the pharmaceutical composition of the present invention, and the dosage form may be set as appropriate according to the administration method. The dosage form of the pharmaceutical composition of the present invention at the time of administration is, for example, liquid, cream, gel, powder, or the like. Furthermore, the dosage form of the pharmaceutical composition of the present invention before administration, specifically the dosage form during the distribution process may be, for example, the same as or different from the dosage form at the time of administration. In the case of the latter, the dosage form may be, for example, a form that allows a pharmacist, a nurse, a physician, or the like at the time of administration to prepare the pharmaceutical composition into a dosage form for use at the time of administration. The dosage form before administration may be, for example, a powder, a solid such as granules, a concentrated liquid, or the like.

As described above, the additive components to the pharmaceutical composition of the present invention may be set as appropriate according to the administration method, the dosage form, and the like, and examples thereof include a solvent, a diluent, an excipient, and a carrier. The solvent may be, for example, an aqueous solvent such as water, saline solution, isotonic solution, or buffer solution, an oil solvent such as soybean oil, or an emulsion solvent, which is a mixed solution of an aqueous solvent and an oil solvent. The pharmaceutical composition of the present invention may contain, for example, alcohols, polyalcohols, surfactants, and the like, as the additive components. Furthermore, the pharmaceutical composition of the present invention may contain, for example, a DDS agent for effectively delivering the active component to the treatment site. The pharmaceutical composition of the present invention may be, for example, in a form containing a carrier in which the active component is encapsulated. The carrier may be, for example, nanoparticles such as polymers. The form in which the active component is encapsulated in this manner can maintain the stability of the active component, and also allow the carrier to function, for example, as a DDS. In this case, for example, the pharmaceutical composition of the present invention is preferably used for administration, for example, by intravenous injection or the like.

Examples of the administration target (test subject) of the pharmaceutical composition of the present invention include a human and a non-human animal. There is no particular limitation on the administration conditions of the pharmaceutical composition of the present invention, and the administration conditions may be determined as appropriate according to the species, the age, the weight, the sex, the presence or absence of amyloid-β aggregation diseases, the degree of progression, and the like. If the administration target is an adult male weighing 70 kg, the administration conditions of the pharmaceutical composition of the present invention are, for example, such that the total amount of Peptide (Peptide 1 and/or Peptide 2) per administration is 0.0005 to 100 mg, the administration frequency is once per day, and the interval is every 1 to 10 days.

In this specification, as described above, the meaning of treatment includes, for example, the meaning of prevention, inhibition of progression, and amelioration (alleviation). The pharmaceutical composition of the present invention may be used, for example, for any one or more of these purposes.

<Aggregation Inhibiting Method>

As described above, the method for inhibiting amyloid-β aggregation of the present invention is characterized by including adding the amyloid-β aggregation inhibitor of the present invention to a test subject. The inhibiting method of the present invention is characterized by using the aggregation inhibitor of the present invention, and there is no limitation on the other steps, conditions, or the like.

As for the addition of the aggregation inhibitor of the present invention to the test subject, reference can be made to the foregoing descriptions regarding the aggregation inhibitor and the pharmaceutical composition of the present invention. It is preferable that the method for inhibiting aggregation of the present invention further includes, for example, performing incubation, after adding the aggregation inhibitor of the present invention to the test subject. If the test subject is a non-living being, the incubation temperature is, for example, from room temperature to 37° C., the incubation time is from 4 to 72 hours, and the pH is from 6.5 to 8. Also, if the test subject is a cell or tissue, the incubation temperature is, for example, from room temperature to 37° C., the incubation time is from 1 to 7 days, and the pH is from 6.5 to 8.

<Method for Treating Amyloid-β Aggregation Disease>

As described above, the method for treating an amyloid-β aggregation disease of the present invention is characterized by administering the amyloid-β aggregation inhibitor of the present invention to a test subject. The treating method of the present invention is characterized by using the pharmaceutical composition of the present invention, and there is no limitation on the other steps, conditions, or the like.

As for the addition of the aggregation inhibitor of the present invention to the test subject, reference can be made to the foregoing descriptions regarding the aggregation inhibitor and the pharmaceutical composition of the present invention.

<Use of Peptide>

The peptide of the present invention is a peptide having an amino acid sequence of SEQ ID NO: 1 or 2, for use in inhibiting aggregation of amyloid-β. Furthermore, the peptide of the present invention is a peptide having an amino acid sequence of SEQ ID NO: 1 or 2, for use in treating amyloid-β aggregation diseases caused by aggregation of amyloid-β.

EXAMPLES

Example 1

The ability of Peptide 1 (GSGNR (SEQ ID NO: 1)) and Peptide 2 (GSGFK (SEQ ID NO: 2)) to inhibit aggregation of amyloid-β (Aβ) was checked.

(1) Aβ Fragment Peptide

An Aβ-derived fragment peptide was used for aggregation of Aβ. Aβ25-35, which has high aggregability, was selected as the fragment peptide. The Aβ25-35 is a peptide constituted by 11 amino acid residues consisting of the $25^{th}$ to $35^{th}$ amino acid residues in the full length sequence of human-derived Aβ (GSNKGAIIGLM (SEQ ID NO: 4), hereinafter also referred to as Ab25-35).

(2) Aggregation Inhibition Assay

The fluorescent dye thioflavin T (ThT) binds to Ab aggregates and emits strong fluorescence upon binding, and thus the increase or inhibition of aggregation can be determined by measuring the fluorescence intensity. Thus, the inhibition of aggregation of Aβ25-35 by Peptide 1 (GSGNR (SEQ ID NO: 1)) and Peptide 2 (GSGFK (SEQ ID NO: 2)) was checked using ThT.

Specifically, a reaction solution with the following composition was prepared and dispensed into wells such that the amount of the reaction solution per well was 300 μL, and incubated at 37° C., and the change in fluorescence intensity over time was measured using a measurement device (product name Cytation5, manufactured by BioTek) (n=3). The measurement wavelengths were set such that the excitation wavelength (ex) was 444 nm and the emission wavelength (em) was 480 nm. As a control, a reaction solution to which water was added instead of Peptide 1 and Peptide 2 was also measured in the same way.

TABLE 1

| | Amount | Final conc. |
|---|---|---|
| 1 mM Peptide 1 or 2 | 100 uL | 0.1 mM |
| 1 mM Aβ25-35 | 100 uL | 0.1 mM |
| 10 mM ThT | 10 uL | 0.1 mM |
| 100 mM Tris-HCl (pH 7.5) | 500 uL | 50 mM |
| MilliQ | 290 uL | — |
| Total | 1000 uL | — |

FIG. 1 shows the results. FIG. 1 is a graph showing the fluorescence intensities of reaction solutions to which Peptide 1 (GSGNR (SEQ ID NO: 1)) or Peptide 2 (GSGFK (SEQ ID NO: 2)) was added. In FIG. 1, the X axis indicates the incubation time (h), and the vertical axis indicates the fluorescence intensity (unit: Fluorescence Intensity). In the graph, note that Ab means Aβ (the same applies below). As shown in FIG. 1, the fluorescence intensity of the reaction solution containing only Aβ25-35 serving as a negative control increased rapidly from 0 to 4 hours. The fluorescence intensity of the reaction solution containing Aβ25-35 gradually decreased slightly after 4 hours, with this being because the aggregates of Aβ25-35 gradually precipitated and the aggregation was not reflected in the fluorescence intensity. On the other hand, the fluorescence intensity of the reaction solution to which Peptide 2 (GSGFK (SEQ ID NO: 2)) was added (plotted as ×) had slightly increased 4 hours after incubation, but it was well below the negative control. It was found that Peptide 2 can inhibit aggregation, specifically, aggregation, for example, itself of Aβ25-35. Furthermore, the fluorescence intensity of the reaction solution to which Peptide 2 (GSGFK (SEQ ID NO: 2)) was added did not increase after 8 and 24 hours. Also, the fluorescence intensity of the reaction solution to which Peptide 1 (GSGNR (SEQ ID NO: 1)) was added had increased 4 hours after incubation, but decreased significantly compared with the negative control after 8 and 24 hours. It was found that Peptide 1 can inhibit aggregation; specifically, even when Aβ25-35 aggregates, Peptide 1 can dissociate the aggregation.

(3) Concentration Assay

The concentrations of Peptide 1 (GSGNR (SEQ ID NO: 1)) and Peptide 2 (GSGFK (SEQ ID NO: 2)) with respect to Aβ25-35 were checked. Unless otherwise indicated, measurements were performed according to (2) above.

First, as for Peptide 2 (GSGFK (SEQ ID NO: 2)), 200 μL of mixed solution with the composition shown in Table 2 below was added per well, 10 μL of 2 mmol/L ThT was further added to the well immediately before measurement, and this reaction solution was incubated at 37° C. The change in fluorescence intensity 4 hours after the start of measurement was measured using the above-mentioned measurement device (n=3). Furthermore, reaction solutions with the following composition but with different final concentrations of Peptide 2 were also measured in the same way. As a negative control, a reaction solution with the following composition to which neither Peptides 1 nor 2 was added was also measured in the same way.

TABLE 2

| | Amount | Final conc. |
|---|---|---|
| 1 mM Peptide 1 or 2 | 80 uL | 100 μM |
| 1 mM Aβ25-35 | 80 uL | 100 μM |

TABLE 2-continued

|  | Amount | Final conc. |
|---|---|---|
| 10 × PBS | 80 uL | — |
| MilliQ | 560 uL | — |
| Total | 800 uL | — |

Figure 2:
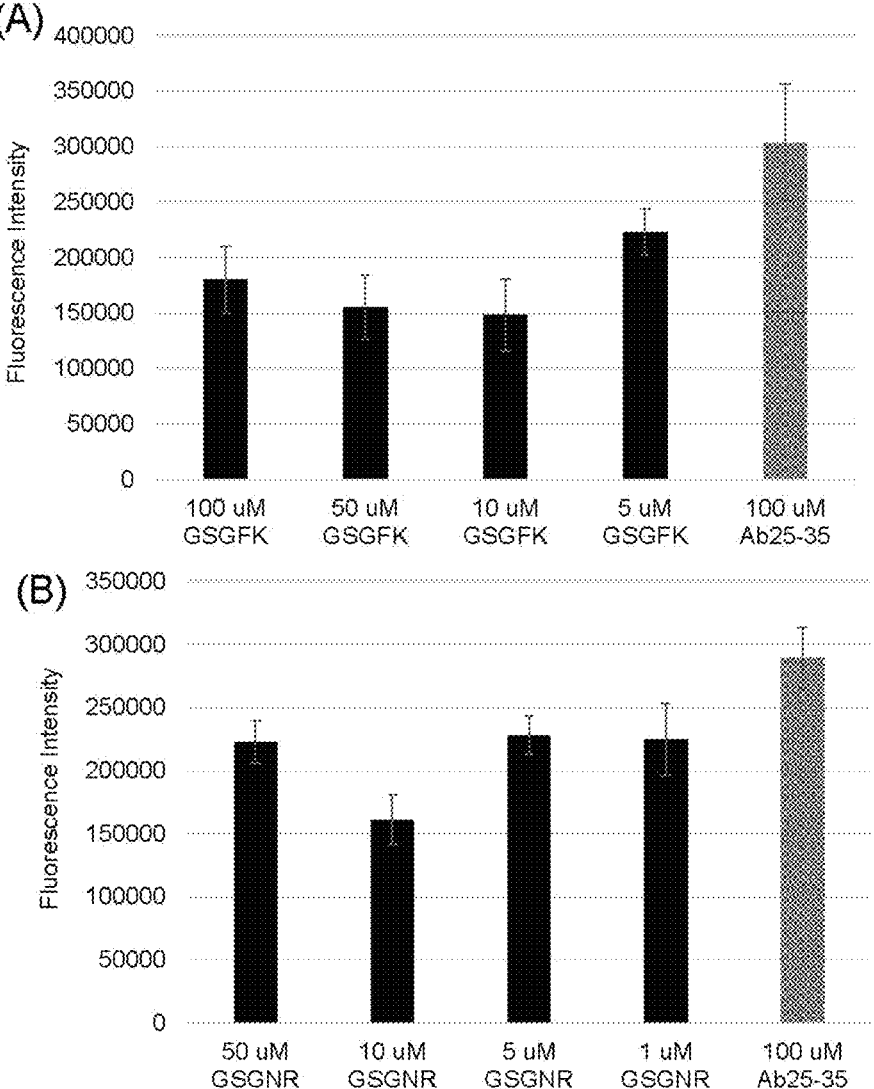
FIG. 2(A) is a graph showing the fluorescence intensities of reaction solutions to which Peptide 2 (GSGFK (SEQ ID NO: 2)) was added.
FIG. 2(B) is a graph showing the fluorescence intensities of reaction solutions to which Peptide 1 (GSGNR (SEQ ID NO: 1)) was added.

FIG. 2(A) shows the results. FIG. 2(A) is a graph showing the fluorescence intensities of reaction solutions to which Peptide 2 (GSGFK (SEQ ID NO: 2)) was added. In FIG. 2(A), the X axis indicates the incubation time (h), and the vertical axis indicates the fluorescence intensity (unit: Fluorescence Intensity). As shown in FIG. 2(A), the addition of Peptide 2 significantly reduced the fluorescence intensity compared with the negative control to which only Aβ25-35 was added, which confirmed that Peptide 2 inhibits aggregation of Aβ25-35. Furthermore, it was found that, with respect to 100 μmol/L of Aβ25-35, Peptide 2 significantly inhibited the aggregation sufficiently when added at a final concentration of 5 μmol/L or more, more effectively inhibited the aggregation when added at a final concentration of 10 μmol/L or more, and inhibited the aggregation in a particularly excellent manner when added at a final concentration of around 10 μmol/L.

Next, as for Peptide 1 (GSGNR (SEQ ID NO: 1)), 200 μL of mixed solution with the composition shown in Table 2 above was added per well, 10 μL of 2 mmol/L ThT was further added to the well immediately before measurement, and this reaction solution was incubated at 37° C. The change in fluorescence intensity 8 hours after the start of measurement was measured using the above-mentioned measurement device (n=6). Furthermore, reaction solutions with the composition above but with different final concentrations of Peptide 1 were also measured in the same way. As a negative control, a reaction solution with the composition above to which neither Peptides 1 nor 2 was added was also measured in the same way.

FIG. 2(B) shows the results. FIG. 2(B) is a graph showing the fluorescence intensities of reaction solutions to which Peptide 1 (GSGNR (SEQ ID NO: 1)) was added. In FIG. 2(B), the X axis indicates the incubation time (h), and the vertical axis indicates the fluorescence intensity (unit: Fluorescence Intensity). As shown in FIG. 2(B), the addition of Peptide 1 significantly reduced the fluorescence intensity compared with the negative control to which only Aβ25-35 was added, which confirmed that Peptide 1 inhibits aggregation of Aβ25-35. Furthermore, it was found that, with respect to 100 μmol/L of Aβ25-35, Peptide 1 significantly inhibited the aggregation sufficiently when added at a final concentration of 1 μmol/L or more, and inhibited the aggregation in a particularly excellent manner when added at a final concentration of around 10 μmol/L.

Example 2

The effect of Peptide 2 (GSGFK (SEQ ID NO: 2)) in vivo was checked. Note that physiological saline was used as a solvent for adjusting peptide or Aβ25-35 for administration.

In this example, 2 μL of 0.5 μg/μL Aβ25-35 and 2 μL of 0.25 μg/μL Peptide 2 were directly administered using a micro syringe to the CA1 area of the hippocampus of the brain of the administration group of C57BL/6 mice (7 to 13 months old) (n=3). In a similar manner, 2 μL of 0.5 μg/μL Aβ25-35 was directly administered using a micro syringe to the CA1 area of the hippocampus of the brain of the negative control group of C57BL/6 mice (n=3). Neither 2 μL of Aβ25-35 nor Peptide 2 was administered to the positive control group of C57BL/6 mice (n=3). Each group was then given a Y-maze (short-term memory assessment) test on days 11, 27, and 39 after administration, and an object recognition test over 3 days starting from day 49.

Administration group (7 months old): Aβ25-35(+)/GSGFK(+)

Negative control group (7 months old): Aβ25-35(+)/GSGFK(−)

Positive control group (13 months old): Aβ25-35(−)/GSGFK(−)

The Y-maze test was conducted in a general manner under the following conditions. That is to say, mice were placed such that their noses faced the wall at an end of one particular arm among the three arms. The mice were allowed to move freely for 10 minutes, and their behavior was captured on a monitor of an analyzer (product name: Time YM1, manufactured by O'hara & Co., Ltd.) to calculate the alternation behavior rate (alternation behavior (%)).

The object recognition test (ORT) from day 49 was conducted as follows. First, for the purpose of checking sociability, mice were placed in a square cage (with a width of 45 cm, a length of 45 cm, and a height of 15 cm) and allowed to become accustomed to the space over the course of one day. For each group, the speed of movement of the mice in the cage was measured, as well as the percentage (%) of time they stayed in the center region of the cage (the inner region being at least 7.5 cm away from a side wall of the cage).

After one day, two identical objects were placed in the cage and the mice were allowed to explore freely for one hour (sample phase). After one hour of exploration, the right side object of the two objects in the cage was replaced by a different object and the mice were again placed in the cage and allowed to explore freely (test phase). Also, the approach time of the mice to each object was measured in each of the sample and test phases. The percentage of the exploration time for the object on the right side with respect to the total exploration time was then determined (100× right side exploration time/total exploration time (%)).

In parallel with the administration to the mice in each group, the fluorescence intensity was measured for the solutions administered to each group. Specifically, a mixed solution obtained by mixing 0.5 μg/μL Aβ25-35 and 0.25 μg/μL Peptide 2 in equal amounts, which was the same as that administered to the administration group, and a 0.5 μg/μL Aβ25-35 solution, which was the same as that administered to the negative control group, were each added in an amount of 100 μL per well, and 10 μL of 1 mmol/L ThT was further added to the well immediately before measurement. These reaction solutions were each reacted at 37° C., and the fluorescence intensity was measured as in Example 1 above.

Figure 3:
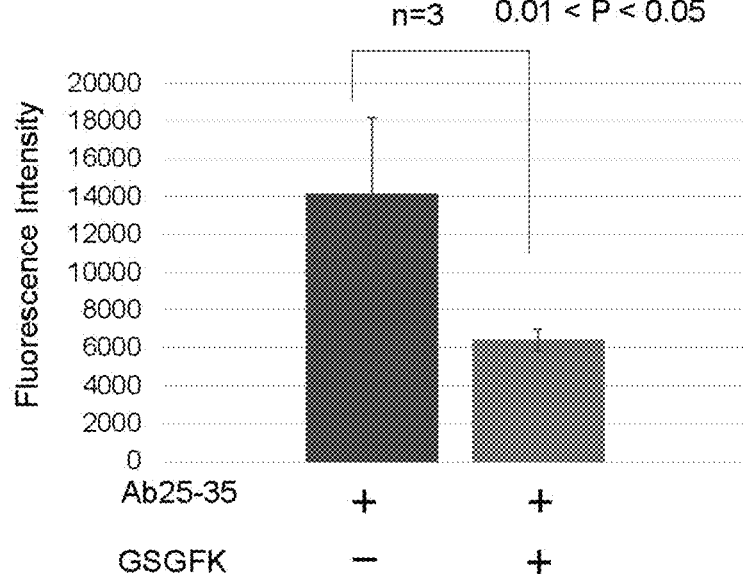
FIG. 3 is a graph showing the fluorescence intensities of an Aβ25-35 solution and an Aβ25-35/Peptide 2 mixed solution on day 11.

FIG. 3 shows the measurement results of fluorescence intensities of the Aβ25-35 solution and the mixed solution on day 11. In FIG. 3, Aβ25-35(+)/GSGFK(−) indicates the measurement results of the Aβ25-35 solution, and Aβ25-35(+)/GSGFK(+) indicates the measurement results of the mixed solution. In FIG. 3, the vertical axis indicates the fluorescence intensity (unit: Fluorescence Intensity). As shown in FIG. 3, on day 11, the Aβ25-35 solution showed an increase in fluorescence intensity indicating aggregation of Aβ25-35, whereas the mixed solution containing Peptide 2 did not show an increase in fluorescence intensity. That is to say it is clear from these results that Aβ25-35 aggregates in vitro and that the aggregation is inhibited by the presence of Peptide 2.

Figure 4:
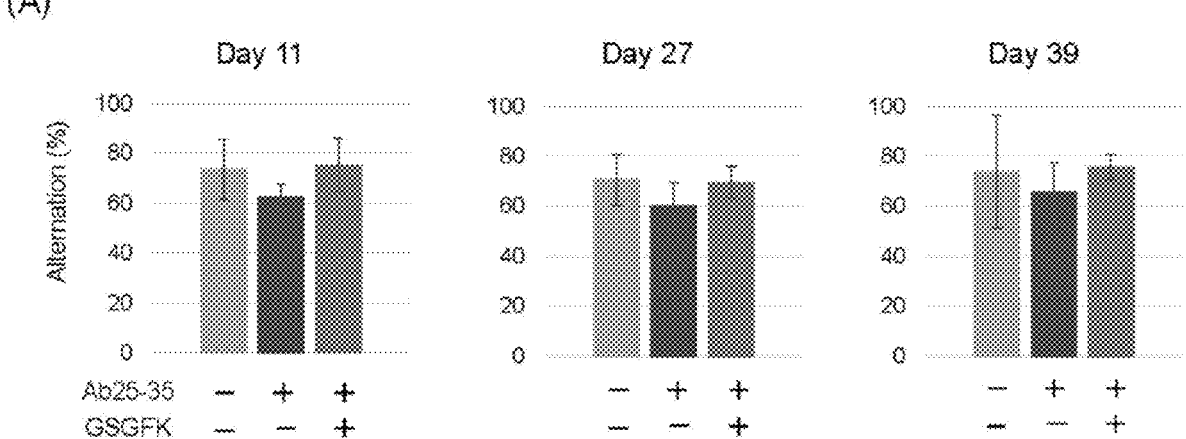
FIG. 4(A) is a bar graph showing the alternation behavior rates of mouse groups.
FIG. 4(B) is a line graph showing the alternation behavior rates of mouse groups.
Figure 4:
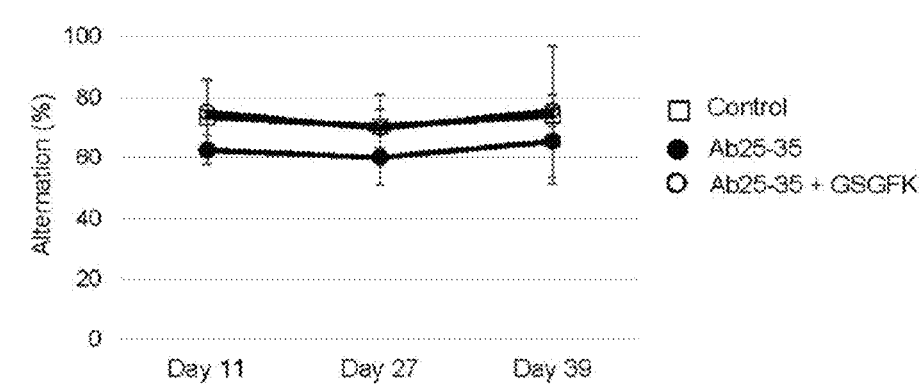

FIGS. 4(A) and 4(B) show the results of the Y-maze test on days 11, 27, and 39. FIG. 4(A) is a bar graph showing the alternation behavior rate of each group, and FIG. 4(B) is a line graph showing the alternation behavior rate of each group, where the vertical axes each indicate the alternation behavior rate (alternation behavior (%)). As shown in FIG. 4, on day 11, the negative control group to which only Ab25-35 was added showed a significantly lower alternation behavior rate than the positive control group and the administration group, and this result was maintained on subsequent days 27 and 39 as well. It is known that the formation of Aβ aggregates in the brain results in a decline in short-term memory and cognitive function. Thus, it is proven from the results of aggregation of Aβ25-35 shown in FIG. 3 above and the results of short-term memory shown in FIG. 5 that administration of Ab25-35 alone causes aggregation of Aβ25-35 and a decline in short-term memory whereas, in the presence of Peptide 2, aggregation of Aβ25-35 is inhibited, as a result of which short-term memory is maintained as with the positive control group to which Aβ25-35 was not administered.

Figure 5:
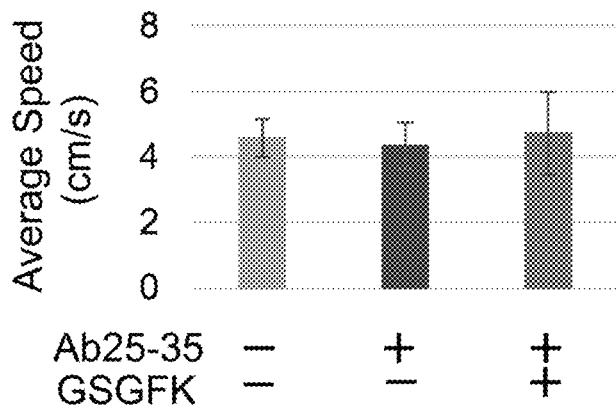
FIG. 5(A) is a graph showing the movement speeds of mouse groups.
FIG. 5(B) is a graph showing the percentages of time mouse groups spent in a center region.
Figure 5:
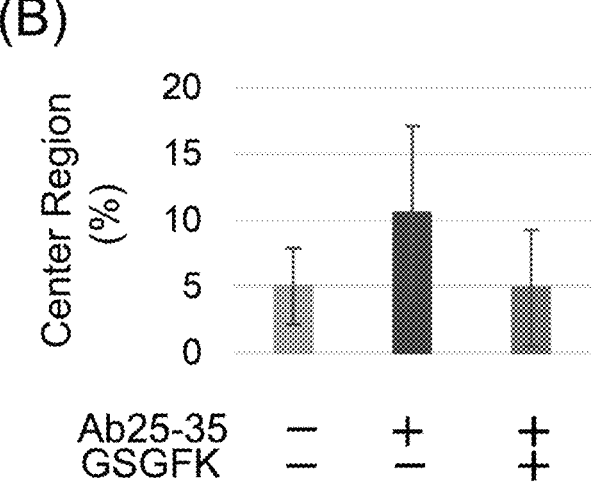

FIG. 5 shows the results of the movement speed and the percentage of time spent in a center region on day 1, which represent the sociability of the mice. FIG. 5(A) is a graph showing the movement speed of each group, where the vertical axis indicates the average speed (cm/s), and FIG. 5(B) is a graph showing the percentage of time spent in a center region, where the vertical axis indicates the percentage (%) of time spent. As shown in FIG. 5(A), there was no difference in movement speed between the groups. Furthermore, as shown in FIG. 5(B), the negative control group to which Aβ25-35 was administered had a slightly higher percentage of time spent than the administration group and the positive control group, which confirmed that they were less fearful than the other groups.

Figure 6:
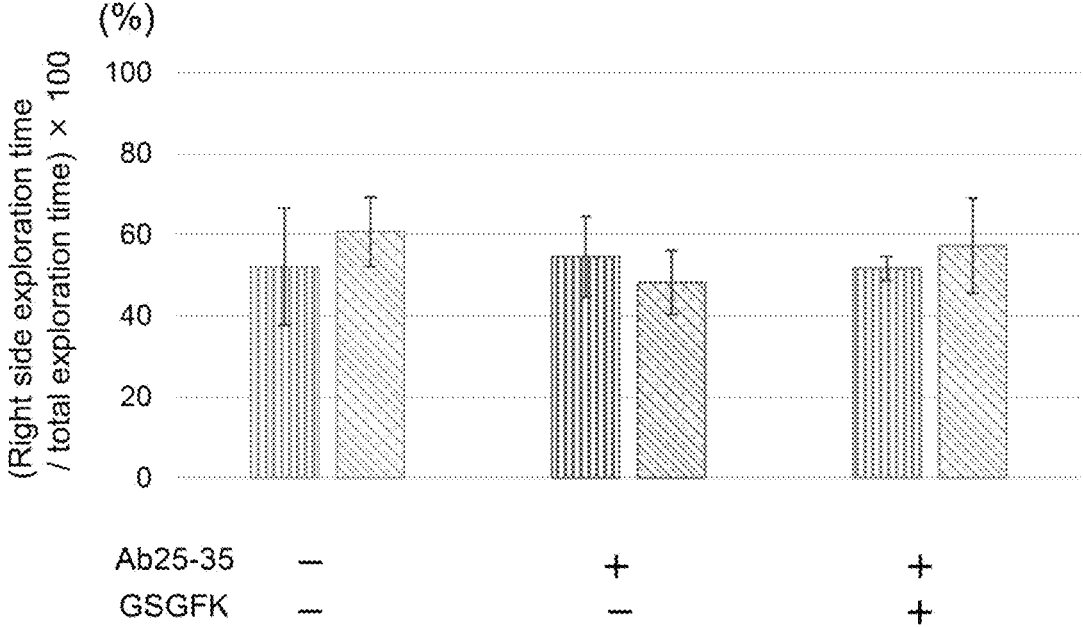
FIG. 6 is a graph showing results of the object recognition test for mouse groups.

FIG. 6 shows the results of the object recognition test on day 52, which was conducted over 3 days from day 49. In FIG. 6, the vertical axis indicates the percentage (%) of the exploration time for the object on the right side with respect to the total exploration time. It is known that the formation of Aβ aggregates in the brain results in a decline in short-term memory making it difficult to recognize objects. Thus, when the object on the right side has been replaced by a different object, mice with a normal short-term memory would recognize that the object has been replaced and explore the new object out of interest, whereas mice with reduced short-term memory would not recognize that the object has been replaced and not be interested in the new object, resulting in no change in the exploration time for the object on the right side. As shown in FIG. 6, the positive control group and the administration group to which Aβ25-35 and Peptide 2 were added showed a significant increase in the percentage of exploration time for the object on the right side in the test phase (oblique lines) compared with the sample phase (vertical lines). On the other hand, the administration group to which only Aβ25-35 was added did not show a significant increase, and, on the contrary showed a decrease in the percentage of exploration time for the object on the right side in the test phase (oblique lines) compared with the sample phase (vertical lines). That is to say, it can be concluded from these results that the negative control group to which only Aβ25-35 was administered had a decline in short-term memory due to aggregation of Aβ25-35, whereas, in the administration group, Peptide 2 inhibited aggregation of Aβ25-35, and thus short-term memory was maintained as with the positive control group, or a decline in short-term memory was inhibited.

Example 3

The ability of Peptide 1 (GSGNR (SEQ ID NO: 1)) and Peptide 2 (GSGFK (SEQ ID NO: 2)) to dissociate amyloid-β (Aβ) aggregates was checked.

A reaction solution with the following composition was prepared and incubated at 37° C. for 24 hours to form aggregates of Aβ25-35. After incubation, the fluorescence intensities of the reaction solution with the following composition to which Aβ25-35 was added and a reaction solution to which water was added instead of Aβ25-35 were measured as in Example 1. As a result, the fluorescence intensity of the reaction solution to which Aβ25-35 was added significantly increased compared with that of the reaction solution to which Aβ25-35 was not added, and thus it was found that aggregates of Aβ25-35 were formed.

Then, 40 μL of 10 mmol/L Peptide 1 or Peptide 2 was added to 4000 μL of the reaction solution in which the aggregates were formed (0 hr), the mixture was incubated at 37° C., and the change in fluorescence intensity over time was measured (n=3). As a control, a reaction solution to which water was added instead of Peptide 1 and Peptide 2 was also measured at 0 hr in the same way. Then, the percentage (%) of decrease in fluorescence intensity after 4 hr was obtained from the fluorescence intensity at 0 hr.

TABLE 3

| | Amount | Final conc. |
|---|---|---|
| 2 mM Aβ25-35 | 200 uL | 0.1 mM |
| 10 mM ThT | 40 uL | 0.1 mM |
| 100 mM Tris-HCl (pH 7.5) | 2000 uL | 50 mM |
| MilliQ | 1760 uL | — |
| Total | 4000 uL | — |

Figure 7:
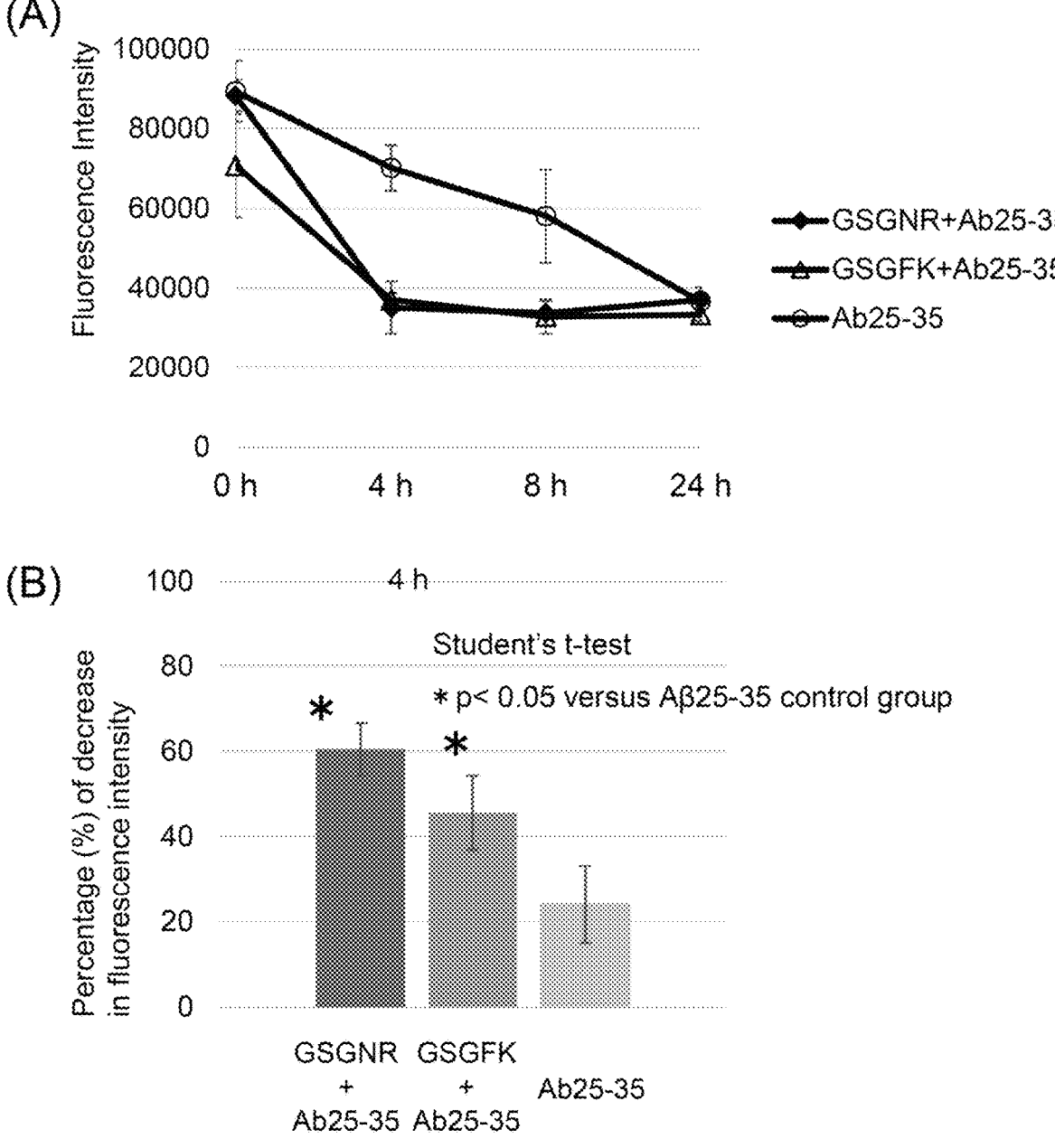
FIG. 7(A) is a graph showing the fluorescence intensities of reaction solutions to which Peptide 1 (GSGNR (SEQ ID NO: 1)) or Peptide 2 (GSGFK (SEQ ID NO: 2)) was added.
FIG. 7(B) is a graph showing the percentages of decrease in fluorescence intensity 4 hours after the peptide was added.

FIG. 7 shows the results. FIG. 7(A) is a graph showing the fluorescence intensities of reaction solutions to which Peptide 1 (GSGNR (SEQ ID NO: 1)) or Peptide 2 (GSGFK (SEQ ID NO: 2)) was added, where the vertical axis indicates the fluorescence intensity (unit: Fluorescence Intensity). FIG. 7(B) is a graph showing the percentages of decrease in fluorescence intensity after 4 hr, where the vertical axis indicates the 15 percentage (%) of decrease in fluorescence intensity. As shown in FIG. 7, it was confirmed that the addition of Peptide 1 or Peptide 2 resulted in a significant decrease in fluorescence intensity 4 hours after the start of incubation. It was confirmed from this result that Peptide 1 and Peptide 2 dissociate Aβ25-35 aggregates. In the negative control to which neither Peptide 1 nor Peptide 2 was added, the fluorescence intensity was time-dependent. However, this decrease in fluorescence intensity was not due to dissociation of the aggregates, but rather to the progression of aggregation, which causes the aggregates to precipitate and lowers the concentration of the aggregates suspended in the reaction system.

In the description above, the present invention was described by way of embodiments and examples, but the invention is not limited to the foregoing embodiments and examples. Various changes that can be understood by those skilled in the art can be made to the configuration and details of the invention within the scope of the invention.

This application claims the benefit of priority from Japanese Patent Application No. 2020-167404, filed on Oct. 2, 2020, the entire contents of which are incorporated herein by reference.

13
INDUSTRIAL APPLICABILITY

The amyloid-β aggregation inhibitor of the present invention can inhibit the aggregation of amyloid-β through intermolecular association, thus enabling treatment, e.g., prevention, inhibition of progression, and amelioration, of amyloid aggregation diseases such as Alzheimer's.

14
2. A method for treating an amyloid-β aggregation disease caused by aggregation of amyloid-β, comprising administering an amyloid-β aggregation inhibitor to a subject in need thereof,
 wherein the amyloid-β aggregation inhibitor is a peptide selected from the group consisting of GSGNR (SEQ ID NO: 1) and GSGFK (SEQ ID NO: 2).

The invention claimed is:

1. A method for inhibiting aggregation of amyloid-β, comprising administering an amyloid-β aggregation inhibitor to a subject in need thereof,
 wherein the amyloid-β aggregation inhibitor is a peptide selected from the group consisting of GSGNR (SEQ ID NO: 1) and GSGFK (SEQ ID NO: 2),
 wherein the subject is a human or a non-human animal.

3. The method according to claim 1, wherein the amyloid-β aggregation inhibitor is included in a pharmaceutical composition comprising the amyloid-β aggregation inhibitor and a pharmaceutically acceptable carrier.

4. The method according to claim 1, wherein the subject in need thereof is suffering from at least one disease selected from the group consisting of memory impairment, Alzheimer's disease, and cerebral amyloid angiopathy.

5. The method according to claim 1, wherein the amyloid-β aggregation inhibitor is administered to the subject prophylactically for an amyloid-β aggregation disease.

6. The method according to claim 3, wherein the pharmaceutical composition further comprises an active component that degrades amyloid-β aggregates that have been formed.

7. The method according to claim 6, wherein the active component that degrades amyloid-β aggregates that have been formed comprises a catalytic peptide that exhibits hydrolytic activity and degrades the amyloid-β aggregates through cleavage thereof.

8. The method according to claim 2, wherein the amyloid-β aggregation inhibitor is included in a pharmaceutical composition comprising the amyloid-β aggregation inhibitor and a pharmaceutically acceptable carrier.

9. The method according to claim 2, wherein the subject in need thereof is suffering from at least one disease selected from the group consisting of memory impairment, Alzheimer's disease, and cerebral amyloid angiopathy.

10. The method according to claim 2, wherein the amyloid-β aggregation inhibitor is administered to the subject prophylactically for an amyloid-β aggregation disease.

11. The method according to claim 8, wherein the pharmaceutical composition further comprises an active component that degrades amyloid-β aggregates that have been formed.

12. The method according to claim 11, wherein the active component that degrades amyloid-β aggregates that have been formed comprises a catalytic peptide that exhibits hydrolytic activity and degrades the amyloid-β aggregates through cleavage thereof.

\* \* \* \* \*

```
                          SEQUENCE LISTING

<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: peptide

<400> SEQUENCE: 1

Gly Ser Gly Asn Arg
1               5

<210> SEQ ID NO 2
<211> LENGTH: 5
<212> TYPE: PRT
<213> ORGANISM: Artificial Sequence
<220> FEATURE:
<223> OTHER INFORMATION: peptide

<400> SEQUENCE: 2

Gly Ser Gly Phe Lys
1               5

<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 11
<212> TYPE: PRT
<213> ORGANISM: Homo sapiens

<400> SEQUENCE: 4

Gly Ser Asn Lys Gly Ala Ile Ile Gly Leu Met
1               5                   10
```